United States Patent [19]

Overath et al.

[11] Patent Number: 5,159,694
[45] Date of Patent: Oct. 27, 1992

[54] PORTABLE REACTOR FOR CARRYING OUT GAS-EVOLVING BIOTECHNOLOGICAL PROCESSES OR GAS CONSUMING PROCESSES WHILE MAINTAINING A PACKED FIXED-BED ARRANGEMENT

[75] Inventors: Horst Overath, Juelich; Carl-Johannes Soeder, Dortmund; Nazir Salhani, Aachen, all of Fed. Rep. of Germany

[73] Assignee: Kernforschungsanlage Juelich GmbH, Juelich, Fed. Rep. of Germany

[21] Appl. No.: 553,357

[22] Filed: Jul. 18, 1990

Related U.S. Application Data

[63] Continuation of Ser. No. 25,746, Mar. 13, 1987, abandoned.

[30] Foreign Application Priority Data

Mar. 14, 1986 [DE] Fed. Rep. of Germany ....... 3608466
Sep. 20, 1986 [DE] Fed. Rep. of Germany ....... 3632093

[51] Int. Cl.$^5$ .................... C12M 1/10; C12M 1/16; C12M 1/40
[52] U.S. Cl. .................... 435/288; 435/299; 435/303; 435/312
[58] Field of Search ............... 435/283–290, 435/299, 303, 310, 312

[56] References Cited

U.S. PATENT DOCUMENTS

| | | | |
|---|---|---|---|
| 3,676,074 | 7/1972 | Shibayama et al. | 435/312 X |
| 4,162,195 | 7/1979 | Solyom et al. | 435/310 |
| 4,286,065 | 8/1981 | Kaluniants et al. | 435/310 X |
| 4,343,904 | 8/1982 | Birch et al. | 435/310 X |
| 4,379,846 | 4/1983 | Shkidchenko et al. | 435/310 X |

FOREIGN PATENT DOCUMENTS

| | | |
|---|---|---|
| 0164888 | 12/1985 | European Pat. Off. |
| PS 673066 | 2/1939 | Fed. Rep. of Germany |
| 673066 | 3/1939 | Fed. Rep. of Germany |
| AS 1033684 | 7/1958 | Fed. Rep. of Germany |
| 1329738 | 5/1963 | France |
| 2528030 | 12/1983 | France |
| 59-55184 | 3/1984 | Japan |
| 929315 | 6/1963 | United Kingdom |
| WO86/03481 | 6/1986 | World Int. Prop. O. |

*Primary Examiner*—Robert J. Hill, Jr.
*Attorney, Agent, or Firm*—Foley & Lardner

[57] ABSTRACT

The coalescence and release of bubbles from packing that supports the growth of microorganisms is promoted by mechanical action on the packed bed arrangement, in particular by continuous or intermittent vibrations, rotations, or by rocking motions. With particular advantage, a reactor vessel which is typically tubular is filled with packing upon which microbial growth is sustained, preferably leaving a free space of 10% to 35%, in particular 15% to 20%. The reactor vessel has an axis that is substantially horizontal but preferably inclined by at least about 3°, and is set continuously or intermittently, for example, by an axle drive or by means of friction wheel drive, into rotational or rocking motions about that axis. The gas can be discharged, for example, via valves and a cam mechanism. Alternatively, a vent pipe, taken through the hollow shaft on the discharge side and upwards, can be provided behind a screen plate. Pipes that are parallel to the axis and that have openings, which are protected by finlike rims with slots, feed liquid or gas to the biomass-containing system in the reaction vessel. In another embodiment, a vertical reactor is equipped with packing provided on vibrating plates which are set into vibration, preferably intermittently. For denitrification, a nitrate-nitrite degradation stage can be provided upstream of the reactor vessel.

25 Claims, 4 Drawing Sheets

PORTABLE REACTOR FOR CARRYING OUT GAS-EVOLVING BIOTECHNOLOGICAL PROCESSES OR GAS CONSUMING PROCESSES WHILE MAINTAINING A PACKED FIXED-BED ARRANGEMENT

This application is a continuation of application Ser. No. 07/025,746, filed Mar. 13, 1987, now abandoned.

BACKGROUND OF THE INVENTION

The present invention relates to a procedure for carrying out biotechnological processes that involve the microbial evolution of gas and that take place in reactors containing granular carriers or particles which support growth of microorganisms. The present invention further relates to equipment for carrying out the procedure in a reactor vessel provided with liquid feed and discharge and with means for the taking off and, if appropriate, the feeding in of gas.

Numerous biotechnological processes take place with the evolution of gas. Methane ($CH_4$) is produced, for instance, in anaerobic degradation processes, and carbon dioxide ($CO_2$) is formed in aerobic fermentation processes. Another example of bioreactions which proceed with gas evolution is bacterial denitrification, wherein nitrate is degraded in the presence of suitable bacteria and organic substances that act as indirect reducing agents under low-oxygen or oxygen-free reaction conditions.

For carrying out these react columnar fixed-bed reactors are frequently used that permanently contain a particulate carrier ("packing") on which growth of bacteria is supported and on which the bacterial reaction takes place. But problems arise when these reactors operate, particularly with increasing reactor size, due to the evolution of gas associated with the bioreaction. The gas formed is released only with delay from the where the growth is sustained; as the reaction proceeds, the delayed release of gas can lead to partial blocking of the active surface occupied by bacteria, and to an increase in the filtration resistance, so that the throughput in the reactor is neither at its optimum level nor at constant rate.

These phenomena have been investigated in more detail for denitrification in fixed-bed reactors where the organic substrate is metered into the nitrate-containing water flowing in or is made available by diffusion out of plastic packing. Nitrogen gas is evolved in the bacterial reaction, and problems arise with the release of the gas from the packed bed occupied by bacteria.

SUMMARY OF THE INVENTION

It is therefore an object of the present invention to provide a procedure for enhancing the release of gas and, thereby, improving the gas-evolving microbial reaction(s), in a biological reactor.

It is also an object of the present invention to provide a biological reactor wherein the release of gas formed in the course of a bioreaction is not delayed, avoiding the blocking problems encountered in conventional reactors.

In accomplishing the foregoing objects, there has been provided, in accordance with one aspect of the present invention, a biological reactor comprising (i) a reactor vessel with a first end, a second end and a major horizontal axis that may be inclined at least 3° to the horizontal, such that the first end is lower than the second end, the reactor having a liquid feed port at the first end and a liquid discharge port at the second end; (ii) a particle bed provided in the vessel for supporting microbial growth; (iii) means for introducing liquid into the vessel through the liquid feed port; (iv) means for removing liquid from the vessel through the liquid discharge port; (v) means for taking off gas from the vessel at the second end; and (vi) means for setting the vessel in motion relative to the major axis. In a preferred embodiment, the bed comprises packing which fills the vessel such that a free space above the packing is created, the free space corresponding to between about 10 and 35% of the total volume of the vessel.

In accordance with another aspect of the present invention, a biological reactor has been provided that comprises (i) a reactor vessel; (ii) a plurality of plates fixed in a predetermined arrangement within the vessel; (iii) granular material supported on the plates, which material can provide a carrier for microbial growth; and (iv) drive means for setting the plates into reciprocating motion.

There has also been provided, in accordance with still another aspect of the present invention, a process comprising the evolution of gas via the action of microorganisms contained in or on a solid support in a biological reactor vessel, wherein the coalescence and release of the bioreaction gas from the support is promoted by setting the support in motion within the reactor vessel. In a preferred embodiment, the motion involved is cyclic, with a cycle time ranging e.g. between about 5 and 25 minutes In another preferred embodiment, the motion comprise intermittent or continuous vibration of the support, preferably in a reciprocating motion with an amplitude of between 5 and 15 mm.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE PREFERRED EMBODIMENTS

In the present invention, the coalescence and release of bioreaction gases from a solid/particulate carrier which supports the microbes is promoted by mechanical action on the substrate within the biological reactor. Typically, the substrate comprises a packed-bed arrangement of grains, plastic spheres or other material upon or within which microorganisms can be immobilized. The bed preferably fills most of the reactor volume, leaving a free space as described in greater detail below. Suitable mechanical action on the substrate in the reactor vessel includes rotation or rocking of the bed; continuous or intermitten vibration of the substrate can also be used, especially in reactors equipped with a series of superposed vibrating plates that provide a base for the packing which carries the bacteria. In any event, the effected displacement of the bed should not be so great as to create a shearing action sufficient to remove biomass that is affixed to the substrate material.

A particularly preferred arrangement with the present invention comprises a generally horizontal packed bed with a longitudinal axis inclined by at least 3°, in particular about 5° to 10°, to the horizontal, which bed is provided in a cylindrical vessel that has perforations for gas release in its upper region; that is not completely filled with packing but has a certain amount of free space above the packing, particularly 10% to 35%, especially 15% to 20%, of the total volume of the vessel; and that is set into a rotary or rocking motion about its longitudinal axis. The rotation or rocking motion (clockwise and anticlockwise by an angle, for example, of 350°, analogously to the motion of washing machine drums) can take place continuously or intermittently, that is, with appropriate pauses. Cycle times of about 5 to 25 minutes, and speeds of rotation between about 0.2 to 10 rpm, are suitable, as is an axle or friction wheel drive which acts on the outer shell of the reactor vessel.

A biological reactor within the present invention can also include suitable gas-discharge means, preferably in the form of at least one gas discharge opening, situated at the higher end of the reactor vessel, with a valve element (particularly a conical valve with a closing spring) for closing the opening, in combination with devices, such as a cam mechanism, for clearing the openings when they pass the highest points.

A reactor of the present invention preferably has axial conduits or hollow shafts for liquid feed and discharge, with an outlet sufficiently raised beyond the reactor that the liquid level in the reactor vessel defines the gas-collection space. For gas discharge, a gas discharge pipe can be used that passes through the hollow shaft and that, in the reactor vessel, leads upwards behind a separating, end-face screen plate. Otherwise the liquid outlet could lead sufficiently far up into the reactor that gas could escape together with the liquid.

In such a reactor, the packing of the fixed bed, which packing supports the microorganisms, while leaving a free space in the reactor, is moved by slow rotation in such a way that gas bubbles do not adhere for any length of time and the gas collects at the highest point in the reactor. The gas can then be discharged from that highest point, continuously or intermittently.

Conduits which are parallel to the axis of the reactor and which have openings, slots or nozzles are preferably arranged along the inner wall of the reactor and are especially protected by fin-like projections equipped with slots. The conduits can also be arranged and protected behind a screen jacket in front of the packed bed. Through such conduits, the liquid to be treated can be fed in and distributed across the surface of the screen jacket. In a preferred embodiment, a rotary tube reactor within the present invention which is provided with protected pipes is used for carrying out gas-consuming biotechnological processes that consume oxygen, such as, for example, for conventional production of acetic acid from ethanol, for the production of amino acids using Corynebacterium glutamicum, and for aerobic effluent treatment. Surprisingly, it has been found that, by feeding oxygen in this way via conduits along the cylindrical wall, a particularly intensive introduction of oxygen can be achieved in a reactor of the present invention, an effect that is not achievable with other, known arrangements for efficiently stirring in or admixing oxygen.

The liquid, delivered by means of a pump or via a suitable level difference, enters via the hollow axis at the lower end of the reactor, preferably through a screen, into the fixed bed in which the microbial conversion of material takes place. By virtue of the displacement (rotation or rocking) of the reactor vessel, which is preferably cylindrical, the bed within the vessel is in continuous or intermittent motion. This motion can be assisted, without slip, by longitudinal fins which confer increased stiffness to the inner wall of the reactor of the present invention.

After a suitable residence time, which is adjusted to the desired degree of conversion or purification performance, the treated liquid leaves the reactor through the second hollow shaft via a screen. In a preferred embodiment, the two hollow shafts are rigid and joined to the reactor vessel by water-proof bearings, and are extended by the liquid feed and discharge lines. Of these lines, especially the discharge line reaches up to a height sufficient for setting the liquid level in the reactor vessel, while leaving a residual free volume in which the gas formed can collect.

According to another preferred embodiment of the present invention, the reactor vessel is an inclined rotary tube that contains packing and is provided with a circle of gas discharge slots or openings at the higher end of the tube. The slots or openings preferably extend over about 5% to 10% of the bed length and follow the generatrices of the rotary tube. The rotary tube of this embodiment is mounted at the end face in a somewhat larger, fixed cylindrical shell which has a gas discharge branch at the upper end and, on the same end face, a liquid outlet located below the gas outlet branch. In this way, the rotary tube containing the packed bed "floats" in a liquid shell, whereby the energy consumption for the rotation is reduced.

Figure 1:
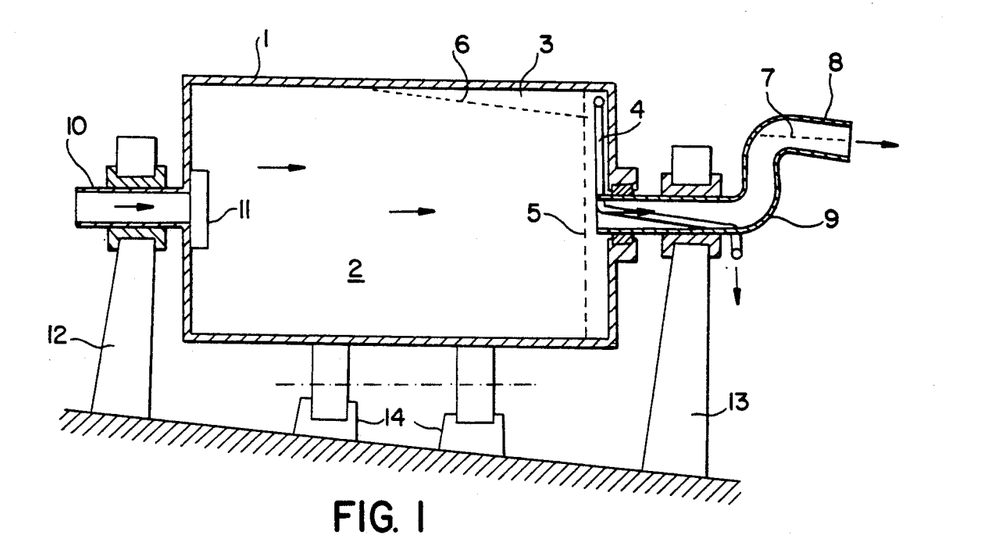
FIG. 1 shows one embodiment of the present invention, comprising an inclined, rotatable, tubular reactor vessel and an upward-leading gas discharge pipe within the vessel behind a screen plate.
Figure 1A:
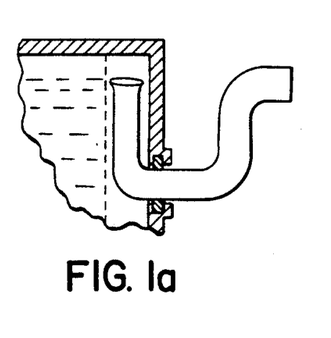

With reference to FIG. 1, a tubular vessel 1 is largely filled by microbial growth-supporting packing 2, leaving a residual free volume 3 where there collects gas formed during the biological process effected by the microorganisms contained in and on the packing. The gas thus evolved can escape via a pipe 4 behind a screen 5 or alternatively via the liquid discharge pipe extending far up into the reactor as may be seen from the outline FIG. 1a. the screen must therefore permit the passage of liquid while retaining the carrier material (solid grains, spheres, etc.) of the bed. Screens produced from plates with apertures on the order of 5 mm have proved suitable in this regard; perforated sheets of sufficient mechanical strength can also be used.

Line 6 indicates the liquid level in the inclined reactor, which level corresponds to outflow level 7, established in the upward-leading extended line 8 of conduit 9 on the outflow side. On the feed side, a conduit 10 is similarly connected rigidly to the reactor tube and, via a rotational joint (not shown), to a feed line.

Optional screens 5 and 11, which in addition optionally may fulfill a deflecting function with regard to the entering liquid, close the tube space off from the hollow shafts, which are mounted in bearing blocks 12, 13. A support bearing with drum drive is indicated by 14.

Figure 2:
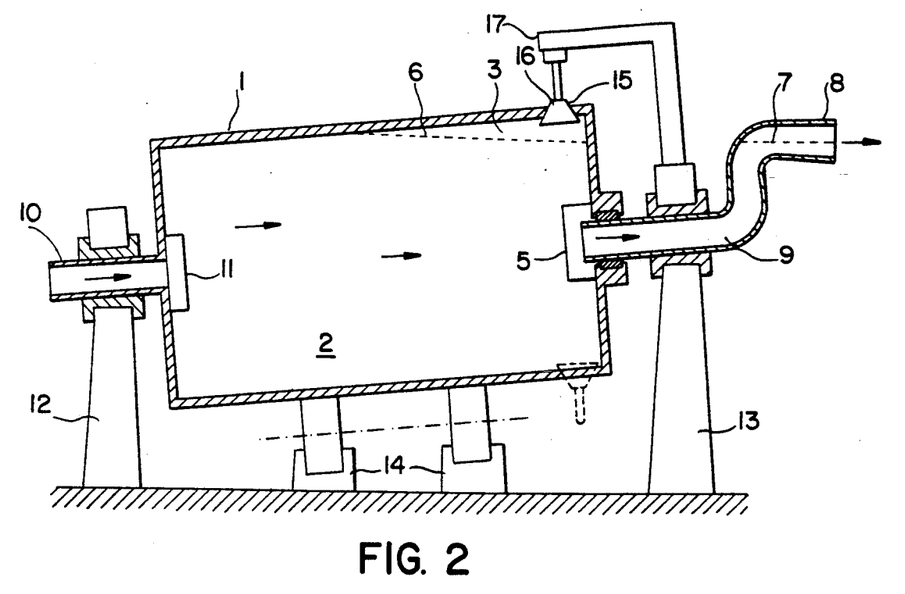
FIG. 2 shows a reactor similar to that depicted in FIG. 1, with gas discharge openings which are gated by valves.

The apparatus shown in FIG. 2 is similar to that of FIG. 1, but is provided with a circle of gated openings 15 for gas discharge. For each opening, a valve cone 16 is pressed against the valve seat (opening 15) by means of a valve spring, not shown. When passing its highest point, the valve cone 16 is lifted from seat 15 by a cam mechanism 17, i.e., the stem of the valve cone is moved downward, allowing gas to escape via opening 15. In FIG. 2, moreover, screen 5 extends over the inlet to conduit 9 only, rather than across the entire cross section of the reaction vessel, as shown FIG. 1.

The rotatable reactor vessel depicted in FIG. 1 or FIG. 2 can be provided on its inner wall with longitudinal fins which ensure that a quantity of material is taken along during the rotary motion. It is preferable that these fins be relatively flat, and that their extent not exceed 10% of the reactor radius.

Figure 3:
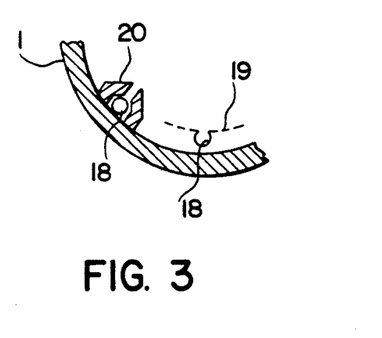
FIG. 3 shows a closeup perspective of an arrangement of longitudinal pipes along the inner cylinder wall of a reactor vessel within the present invention.

According to a preferred embodiment of the present invention which can be used in major installations, pipes 18 are provided (see FIG. 3) that have openings, distributed along their length, for feeding liquid or, when reactions with gas absorption are carried out, for feeding gas, particularly air. The pipes 18 are situated along the inner wall of the reactor vessel, and are screened from the packed bed, for instance, by a support screen 19 parallel to the reactor wall or by projections 20 that define slotted housing for each pipe, as indicated in FIG. 3.

Figure 4:
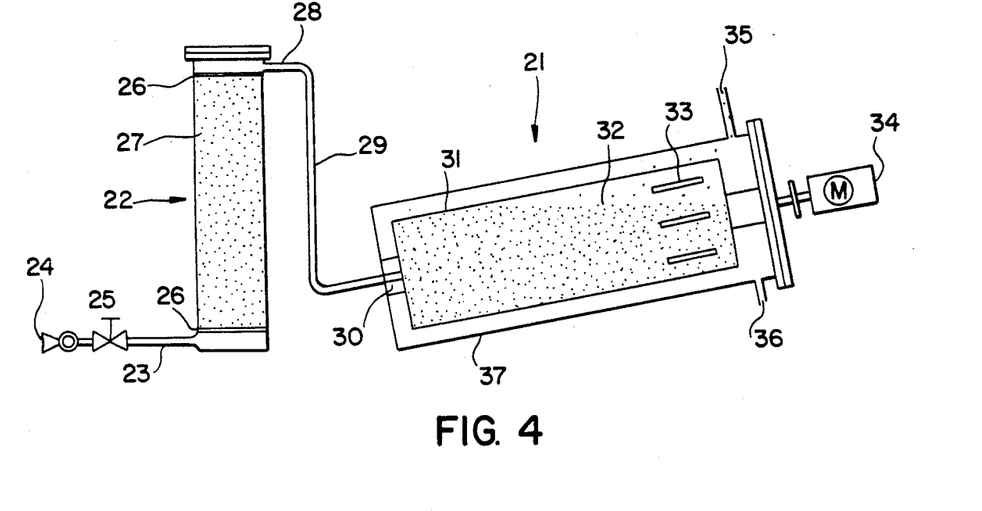
FIG. 4 shows another embodiment of the present invention, comprising a "floating" reactor combined with an upstream denitrification stage.

FIG. 4 depicts an embodiment of the present invention, suitable especially for smaller units, wherein reactor vessel 21 is combined with an upstream vertical column reactor 22. The latter reactor is continuously fed at 23 with nitrate-containing water, by means of a feed pump 24, via a control valve 25 for precise regulation of the water flow rate. Between sieve trays 26, the column reactor 22 contains packing 27, for example, inert plastic granules such as Nitrex ® filter material, or another suitable packing which, due to its porous or rough surface structure, provides favorable settlement zones for the denitrification bacteria. At the column reactor 22, the first degradation stage is initiated, in which the nitrate is largely reduced bacterially to nitrite or the water is freed of oxygen.

The flow rate of the water is controlled such that a high nitrite content is measurable in the outflow 28 from the column reactor 22, and no formation of gas bubbles is observable in the upper third of the reactor.

Via the connecting pipe 29, the water is passed on into the rotatable reactor 21. Through a hollow shaft 30 with a rotational joint and bearing, the water passes into the rotatable inner reactor vessel 31, about 75% of which is filled with granules 32, which provide a support for growth of denitrification bacteria. The second denitrification step takes place anaerobically, nitrogen gas ($N_2$) and/or nitrous oxide ($N_2O$) being formed. Thus, mainly gaseous nitrogen is released as the final stage of the denitrification (nitrate-nitrite respiration) process, which gas escapes from the gas release slots 33, provided in the upper region of the inner vessel 31, into the air, which normally contains about 80% by volume of nitrogen.

In order to avoid the adhesion of gas bubbles to the surface of the packing 32, which adhesion inhibits the activity of the bacteria, the inner vessel 31 is rotated continuously, or intermittently (at up to 15 minute intervals with about 3 minutes rotation), by means of the motor 34 at 0.2 to 3 rpm. It is not absolutely necessary to move the rotatable reactor vessel continuously about it longitudinal axis. If maximum throughput is not important, the inner vessel 31 is set in rotation, for example, every 15 minutes. This step is at the same time favored by the preferably inclined mounting of the reactor at an angle of at least 3°, especially 5° to 15°. The nitrogen gas can finally leave the apparatus via the gas discharge line 35. The water, low in nitrate, can then likewise be taken off from the apparatus via the water outflow 36 in the shell 37.

In the operation of a reactor within the present invention, the continuous gas release from the pore spaces of the bed, or from the apparatus via the gas discharge openings, allows undisturbed bacterial growth on the matrix surface. Moreover, undisturbed water flow is ensured on the surfaces of the packing, where the degradation activity of the denitrification bacteria primarily takes place. Channeling within the reactor vessel, which would impede contact between water and the bacteria on the matrix surface, does not arise here. A particular technological advantage is realized with the substantial spatial separation of the nitrate degradation into two stages, with optimization of the residence times in the reactors 21 and 22 so that, preferentially, only the nitrate degradation to nitrite takes place in the column reactor 22, without bubble formation or reduction of the oxygen content to zero, whereas the nitrite is then degraded to in the rotatable reactor vessel 21.

Figure 5:
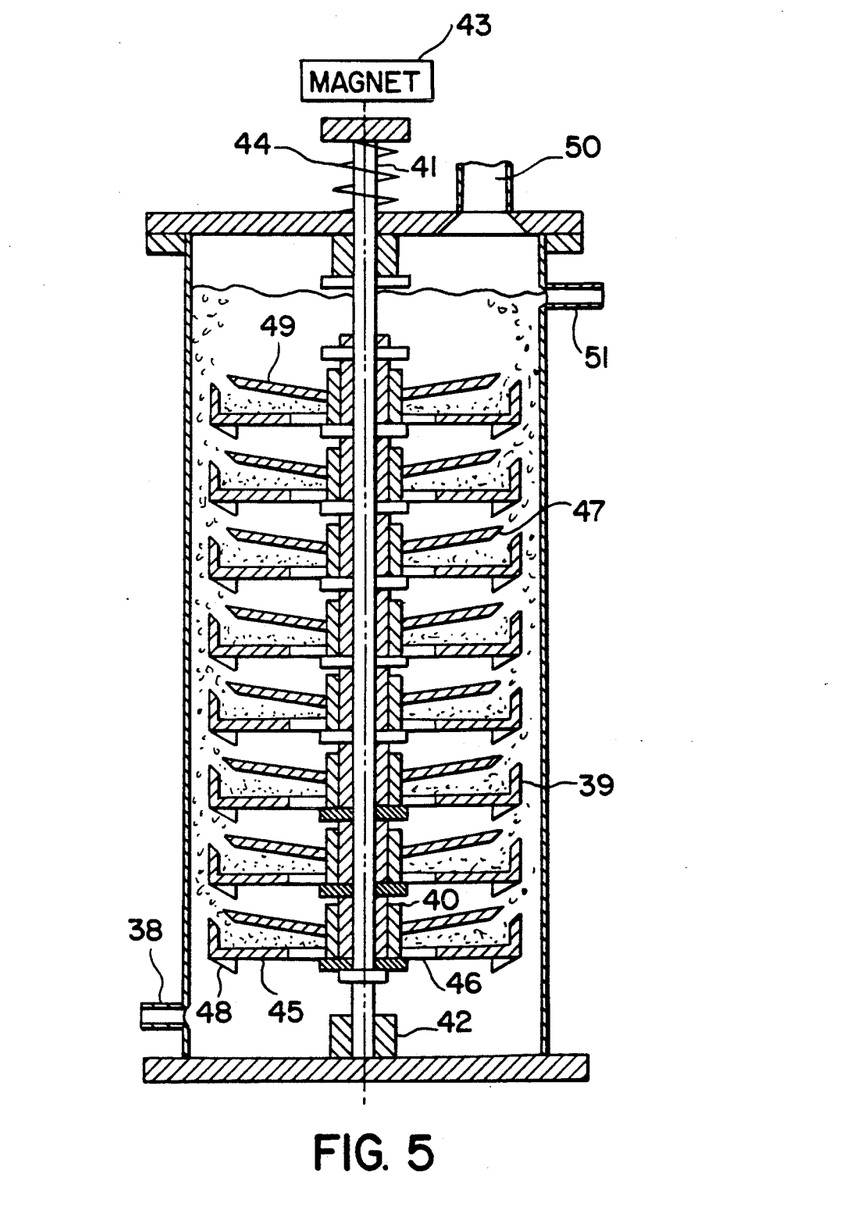
FIG. 5 shows a vibrating-plate reactor in accordance with another embodiment of the present invention.

In the vibrating-plate column reactor shown in FIG. 5, nitrate-containing water is delivered into the reactor space, by means of a feed pump or a hydrostatic pressure difference under valve control, via the inlet 38. The reactor is fitted with a number of reactor chambers 39 (eight are shown) that avoids undue loading of the surface of individual vibrating plate, which are arranged one above the other and which function as a fixed bed. The vibrating plates are mounted to the central axis 41 by means of hollow bushes 40; the central axis is, in turn, guided in a bearing block 42. A solenoid 43 and a compression spring 44 enable the reactor chambers to be set into vertical vibrations via the central axis.

In operating a reactor according to the present invention, the chambers of the reactor can be charged with suitable packing 45 which, due to its surface structure, provides an optimum settling zone for the denitrification bacteria. At the bottom of the chamber, in the section 46, openings extending radially from the center outward are provided, which allow the water that is to be denitrified to flow unhindered into the reactor chamber.

The gas bubbles, formed in the course of the denitrification process on the active packing/bacteria contact surface, can escape along the gas discharge channel 48 via the gas outlet 47 from the reaction spaces. To avoid any possible adhesion of the gas bubbles to the packing, the reactor chambers are set into vibrations via the central axis, whereby the gas bubbles are led off without any problems along the obliquely arranged chamber covers 49. The gas bubbles rising in this way from the individual chamber spaces can then leave the reactor space via the opening 50. The treated water is taken off via the outflow 51.

The bacterial denitrification in a movable, inclined packed bed which supports a growth of bacteria is also suitable for the regeneration of water, particularly seawater from aquaria or from intensive farming of aquatic animals.

What is claimed is:

1. A biological reactor for carrying out a microbiological reaction which produces a gas, comprising (i) a reactor vessel with a first end, a second end and a major horizontal axis, said reactor having a liquid feed port at said first end and a liquid discharge port at said second end; (ii) a solids carrier particle bed provided in said vessel for supporting microbial growth, said solids carrier particle bed filling at least 65% of the total volume of said vessel such that a space remains between said solids carrier particle bed and an internal wall of said reactor vessel; (iii) means for introducing liquid into said reactor vessel through said liquid feed port, said means (iii) comprising a first conduit that opens to said liquid feed port and that is positioned parallel to said major horizontal axis; (iv) means for removing liquid from said reactor vessel through said liquid discharge port, said means (iv) comprising a second conduit that opens to said liquid discharge port and that is positioned parallel to said major horizontal axis; (v) means for taking off gas from said reactor vessel at said second end; and (vi) means for imparting to said bed a rotating or rocking motion around said major axis such that gas produced by said microbiological reaction rises into said space, and said solids carrier particle bed remains in a packed state.

2. A biological reactor as claimed in claim 1, further comprising means for feeding gas into said vessel.

3. A biological reactor as claimed in claim 1, wherein said motion is an intermittent motion.

4. A biological reactor as claimed in claim 1, wherein said particle bed fills said vessel such that a free space above said packing is created, said free space corresponding to between about 10 and 35% of the total volume of said vessel.

5. A biological reactor as claimed in claim 4, wherein said free space corresponds to between about 155 and 20% of said total volume.

6. A biological reactor as claimed in claim 4, wherein said bed is comprised of elements selected from the group consisting of granules and spheres.

7. A biological reactor as claimed in claim 1, wherein means (vi) comprises drive means for rotating or rocking said reactor vessel.

8. A biological reactor as claimed in claim 7, wherein said drive means comprises a support bearing connected with a drum drive.

9. A biological reactor as claimed in claim 1, wherein said means (iv) comprises a bent conduit sufficiently raised beyond the reactor that the liquid level in the reactor vessel defines the space between the solids carrier particle bed and the reactor and which leads sufficiently far up into the reactor that the gas taken off from said reactor vessel at said second end can escape together with the liquid removed from said reactor vessel through said liquid discharge port.

10. A biological reactor as claimed in claim 9, wherein means (v) comprises a conduit with a plurality of openings of the vessel wall at said second end, each opening of said plurality being gated by a valve, respectively, and means for opening and closing each valve.

11. A biological reactor as claimed in claim 1, wherein each of said means (iii) and (iv) further comprises screening means for preventing particles in said vessel from entering their respective conduit.

12. A biological reactor as claimed in claim 11, wherein said screening means comprises a liquid-permeable barrier to passage of material comprising said bed, said barrier extending across the entire cross section of said vessel at said second end.

13. A biological reactor as claimed in claim 1, wherein means (iv) comprises a discharge pipe that communicates with said liquid discharge port, said discharge pipe having an outlet that is positioned relative to said vessel such that the level of liquid at said outlet corresponds to the desired level of liquid in said vessel.

14. A biological reactor as claimed in claim 1, wherein means (iii) comprises (a) a feed pipe that communicates with said liquid feed port and (b) screening means for retainment of the bed particles.

15. A biological reactor as claimed in claim 1, wherein said vessel is provided on an inner wall thereof with longitudinal fins that project inwardly.

16. A biological reactor as claimed in claim 1, wherein said vessel comprises a plurality of feed pipes provided in parallel with said major axis along an inner wall of said vessel, each of said feed pipes having openings into said vessel said pipes being arranged as means (iii) or as said means for feeding gas into the vessel.

17. A biological reactor as claimed in claim 16, wherein each of said feed pipes is contained in a slotted housing.

18. A biological reactor as claimed in claim 16, wherein said plurality of feed pipes is separated from the interior of said vessel by a screen which is parallel to said inner wall of said vessel.

19. A biological reactor as claimed in claim 1, further comprising a fixed container vessel in which said reactor vessel is movably mounted.

20. A biological reactor as claimed in claim 19, wherein said container vessel is provided with separate gas-discharge and liquid-discharge parts.

21. A biological reactor as claimed in claim 21, wherein means (v) comprises a plurality of openings provided in said vessel at said second end.

22. A biological reactor as claimed in claim 21, wherein said opening are slots, each having a length corresponding to between about 5% and about 10% of the length of said bed.

23. A biological reactor as claimed in claim 1, wherein means (v) comprises a conduit protected from the bed by a screen which conduit opens into the free space at the second end and leaves the reactor through said liquid discharge port.

24. A biological reactor as claimed in claim 1, wherein said means (iii) and said means (iv) represent the sole means, respectively, for introducing liquid into and discharging liquid from said reactor vessel.

25. A biological reactor for carrying out a microbiological reaction which produces a gas, comprising (i) a reactor vessel with a first end, a second end and a major axis which is inclined at least 3° to the horizontal, such that the first end is lower than the second end, said reactor having a liquid feed port at said first end and a liquid discharge port at said second end; (ii) a solids carrier particle bed provided in said vessel for supporting microbial growth, said solids carrier particle bed filling at least 65% of the total volume of said vessel such that a space remains between said solids carrier particle bed and an internal wall of said reactor vessel; (iii) means for introducing liquid into said reactor vessel through said liquid feed port, said mean (iii) comprising a first conduit that opens to said liquid feed port and this is positioned parallel to said major axis; (iv) means for removing liquid from said reactor vessel discharge port, said means (iv) comprising a second conduit that opens to said liquid discharge port and that is positioned parallel to said major axis: (v) means for taking off gas from said reactor vessel at said second end; and (vi) means for imparting to said bed a rotating or rocking motion around said major axis such that gas produced by said microbiological reaction rises into said space, and said solids carrier particle bed remains in a packed state.

* * * * *

UNITED STATES PATENT AND TRADEMARK OFFICE
CERTIFICATE OF CORRECTION

PATENT NO. : 5,159,694
DATED : October 27, 1992
INVENTOR(S) : Horst OVERATH, et al It is certified that error appears in the above-identified patent and that said Letters Patent is hereby corrected as shown below:

On the title page, Item [54]:
In the title please delete "PORTABLE" and insert --ROTATABLE--.

Column 7:
Claim 5, line 2, delete "155" and insert --15%--.

Signed and Sealed this

Twenty-third Day of November, 1993

Attest:

BRUCE LEHMAN

*Attesting Officer*       *Commissioner of Patents and Trademarks*